United States Patent
Heymann et al.

(10) Patent No.: US 8,277,462 B2
(45) Date of Patent: Oct. 2, 2012

(54) PHACOEMULSIFICATION DEVICE AND METHOD FOR OPERATING THE SAME

(75) Inventors: Manfred Heymann, Heidenheim (DE); Michael Eichler, Aalen (DE); Erik Düver, Oberkochen (DE); Martin Kraus, Hüttlingen (DE)

(73) Assignee: Carl Zeiss Meditec AG, Jena (DE)

( * ) Notice: Subject to any disclaimer, the term of this patent is extended or adjusted under 35 U.S.C. 154(b) by 114 days.

(21) Appl. No.: 12/677,690

(22) PCT Filed: Sep. 10, 2008

(86) PCT No.: PCT/EP2008/007400
§ 371 (c)(1), (2), (4) Date: May 18, 2010

(87) PCT Pub. No.: WO2009/036917
PCT Pub. Date: Mar. 26, 2009

(65) Prior Publication Data
US 2010/0241131 A1    Sep. 23, 2010

(30) Foreign Application Priority Data
Sep. 13, 2007    (DE) .................. 10 2007 043 612

(51) Int. Cl.
*A61F 9/007*    (2006.01)
*A61B 17/32*    (2006.01)
(52) U.S. Cl. ..................... 606/107; 604/22; 606/169
(58) Field of Classification Search .......... 606/107, 606/128, 167, 169, 170, 171; 604/22
See application file for complete search history.

(56) References Cited

U.S. PATENT DOCUMENTS
4,056,761 A * 11/1977 Jacoby et al. ............. 318/116
(Continued)

FOREIGN PATENT DOCUMENTS
DE    699 24 618 T2    3/2006
(Continued)

OTHER PUBLICATIONS
English translation of German Office Action for corresponding DE Appl. No. 10 2007 043 612.4-55, dated Aug. 14, 2008.
(Continued)

*Primary Examiner* — Elizabeth Houston
(74) *Attorney, Agent, or Firm* — Fish & Richardson P.C.

(57) ABSTRACT

The invention relates to a phacoemulsification device, comprising: —a hand piece having a cutting tip for emulsifying a lens, wherein the tool holder is provided with piezoelectric elements for deflecting the cutting tip, —a regulator, the input of which is electrically connected to the tool holder, for receiving an actual value that is proportional to the voltage induced on the piezoelectric elements of the tool holder that is constantly oscillating on the natural frequency thereof, said regulator being suitable for comparing the actual value with a predetermined target value, thus determining an actuating variable, —a power amplifier, the input of which is connected to the regulator in order to receive the actuating variable, and the output of which is connected to the tool holder, wherein the tool holder may be actuated simultaneously with the receipt of the actual value and a power output to the tool holder being able to occur, such that a direct feedback coupling may be attained, thus enabling the tool holder to constantly oscillate at the natural frequency thereof with a deflection of the cutting tip corresponding to the actuating variable.

20 Claims, 7 Drawing Sheets

U.S. PATENT DOCUMENTS

| | | | |
|---|---|---|---|
| 4,271,371 A * | 6/1981 | Furuichi et al. | 310/316.01 |
| 5,180,363 A * | 1/1993 | Idemoto et al. | 604/22 |
| 5,331,951 A | 7/1994 | Kepley | |
| 5,394,047 A | 2/1995 | Scharlack et al. | |
| 5,728,130 A | 3/1998 | Ishikawa et al. | |
| 6,027,515 A | 2/2000 | Cimino | |
| 6,175,180 B1 | 1/2001 | Angelini et al. | |
| 6,203,516 B1 | 3/2001 | Kepley | |
| 6,259,207 B1 | 7/2001 | Kirshner | |
| 6,997,935 B2 | 2/2006 | Anderson et al. | |

FOREIGN PATENT DOCUMENTS

| | | |
|---|---|---|
| DE | 699 23 618 T2 | 4/2006 |
| EP | 0394583 | 10/1990 |

OTHER PUBLICATIONS

European Office Action for corresponding EP 08 801 972.4-1269, dated Dec. 9, 2010.

International Search Report and English Translation, for corresponding PCT Application No. PCT/EP/2008/007400, dated Feb. 18, 2009.

English Translation of the International Preliminary Report on Patentability, for corresponding PCT Application No. PCT/EP2008/007400, dated Apr. 7, 2010.

English translation of the Chinese Office Action for corresponding CN Appl No. 2008-80107191.4, dated Jun. 15, 2011.

* cited by examiner

PHACOEMULSIFICATION DEVICE AND METHOD FOR OPERATING THE SAME

This application is the National Stage of International Application No. PCT/EP2008/007400, filed Sep. 10, 2008, which claims the benefit of German Application No. 10 2007 043 612.4, filed Sep. 13, 2007. International Application No. PCT/EP2008/007400 is incorporated by reference herein in its entirety.

The invention relates to a phacoemulsification apparatus for emulsifying a lens, a method for operating the phacoemulsification apparatus and a phacoemulsification system having such a phacoemulsification apparatus.

Today, operative treatment of a cataract is predominantly performed by means of phacoemulsification. This involves a clouded lens of the eye being broken up (emulsified) into small parts by means of a hollow needle, which oscillates in the ultrasound range, such that said parts can be aspirated by the needle. Next, the operator inserts an artificial lens as a replacement for the lens which has been broken up in this manner. A fundamental module for performing such phacoemulsification is a handpiece containing said hollow needle or else cutting tip. The requisite ultrasound oscillations for breaking up the clouded lens of the eye can be generated by virtue of the handpiece being provided with piezoceramic elements. When a voltage is applied to said piezoceramic elements, the piezoelectric effect allows a change of length to be brought about, so that a needle connected to the piezo ceramic can be deflected in the longitudinal direction.

To achieve the greatest possible amplitudes for the cutting tip, the piezoelectric elements are operated in the region of the resonant frequency of the handpiece. In the zero-load state, the resonant frequency of a handpiece with a cutting tip can be determined very accurately. However, as soon as the cutting tip comes into contact with the lens which is to be emulsified, the mass ratios change, which means that the resonant frequency shifts. To operate such a handpiece as much in the region of the resonant frequency as possible in each case, U.S. Pat. No. 6,997,935 B2 proposes sensing the phase between the applied voltage and the current flow in order to operate the piezoelectric elements and regulating said phase such that the highest possible power is attained on the basis of the equation $P=U*I*\cos\phi$. In order for the factor $\cos\phi$ to adopt the highest possible absolute value, it is necessary for $\cos\phi=1$ or $\phi=0$. Such a situation arises in a resonant case. However, if the resonant frequency shifts on account of a change in the mechanical loading of the cutting tip, for example, the phase angle is $\phi\neq 0$, but rather it is in the range between 0 and $-\pi/2$ or 0 and $+\pi/2$. According to U.S. Pat. No. 6,997,935 B2, when the phase angle $\phi$ has been sensed, the excitation frequency is regulated such that the excitation frequency of the cutting tip matches the natural frequency $\omega_0$.

A cause of the shift in the resonant frequency is not just altered loading by lens fragments (change of mass), but also heating of the handpiece during prolonged operation and ageing of the piezoceramic elements and hence alteration of the physical properties thereof. These parameters may overlap in any form, so that permanent readjustments are necessary. Advantages of such a method are the relatively simple design of an associated amplifier (digital amplifier) and the uncomplicated determination of the phase angle. However, a drawback is the relatively slow regulation, since determination of the phase angle constantly requires the sensing of a plurality of successive measuring points for the voltage and current profile over time. Furthermore, it is never possible to achieve the resonant case exactly, in principle. The cutting tip is always operated at forced oscillation, which never exactly corresponds to the natural frequency of the handpiece. Although the frequency difference may be small, the accompanying reactive power is relatively high, since the mechanical power is in square proportion to the frequency. The supplied electrical energy is therefore not optimally transformed into a mechanical energy and hence into the maximum amplitude of the cutting tip. In addition, the disturbance variables such as change of mass, heating, ageing and production tolerances are independent of one another, which means that even when a handpiece has been produced ever so carefully it is, in principle, never possible to ensure that during operation of the handpiece the operating frequency is the same as the natural frequency. In general, this means less than optimum operation of the handpiece, which is reflected in a relatively high proportion of reactive power.

It is therefore the object of the invention to propose a phacoemulsification apparatus and a method for operating such an apparatus and also a phacoemulsification system having such an apparatus, wherein the smallest possible proportion of reactive power arises during the emulsification process, so that a higher level of efficiency is obtained than in previously known phacoemulsification apparatuses.

The object is achieved by an apparatus according to independent claim 1, a method according to claim 10 and a system according to claim 16. Advantageous embodiments are described in the subclaims.

The phacoemulsification apparatus according to the invention has:

a handpiece which has a cutting tip for emulsifying a lens, wherein the handpiece is provided with piezoelectric elements for deflecting the cutting tip; a regulator, the input of which is electrically connected to the handpiece in order to receive an actual value which is proportional to the voltage, induced on the piezoelectric elements, of the handpiece constantly oscillating at the natural frequency, wherein the regulator is suitable for comparing the actual value with a prescribed target value and hence determining a controlled variable; a power amplifier, the input of which is connected to the regulator in order to receive the controlled variable, and the output of which is connected to the handpiece, wherein at the same time as the actual value is received the handpiece can be actuated and power can be output to the handpiece, so that direct feedback can be achieved and hence the handpiece can constantly oscillate at the natural frequency thereof with deflection of the cutting tip in line with the controlled variable.

By tapping off and amplifying the induced voltage of the handpiece oscillating at the natural frequency, the amplitude of the cutting tip oscillating at the natural frequency is increased. Such an apparatus therefore oscillates autonomously at the natural frequency, even when it is influenced by external influences, such as a change of mass in the lens fragments, or by internal influences, such as heating of the piezo ceramics. The disturbance variables merely result in the natural frequency shifting, with the system nevertheless continuing to oscillate always at the natural frequency. In this context, what is significant is that an actual value is sensed and at the same time the handpiece can be actuated. There is therefore no sensing mode in which the handpiece is switched off. During sensing of an actual value, the handpiece is supplied with a target variable constantly and without interruption, and hence an output of power to the handpiece is attained. This means that it is possible to achieve direct feedback, where an output variable from the handpiece, that is to say the actual value, can be supplied directly to the input of the regulator. In the switched-on state, the handpiece is always actuated, and in this state an actual value for the voltage induced on the piezoelectric elements is always sensed. Such regulation is very fast, since it is now not necessary to sense a phase angle. The reactive power can be significantly reduced, which means that a higher level of efficiency is achieved.

Preferably, the regulator and the handpiece have a transformer arranged between them, the input of which is connected to the handpiece and the output of which is connected to the regulator. The transformer allows high-quality signal transmission, and at the same time it is possible for the voltage at the output thereof to be significantly lower than at the input thereof. Since the piezo ceramics are often operated in the high-voltage range (up to 1000 V), the use of such a transformer allows DC-isolated transformation in the low-voltage range to be attained.

The phacoemulsification apparatus may also be in a form such that the piezoelectric elements can be excited by an electrical pulse such that a larger oscillation amplitude for the cutting tip is achieved in comparison with white noise. The basis for this development is that the handpiece and the cutting tip oscillate at their natural frequency even without a supply of energy, but the amplitude is very small. In this case, the handpiece oscillates in what is known as "white noise" at its natural frequency. At the start of a regulatory process, the additional electrical pulses allow the amplitude of the cutting tip to be increased such that the induced voltage reaches a sufficiently high absolute value in order to be easily processible by the regulator.

Preferably, the energy supplied by the amplifier can be repeatedly interrupted completely, so that a respective particular time is followed by a quiescent phase. Since, during the emulsification, the lens and other parts coming into contact with the cutting tip, such as the cornea, are heated on account of the ultrasonic oscillations, an excessive temperature can cause damage to the eye. In some cases, cornea burn may arise. The energy supplied to the inventive phacoemulsification apparatus at maximum efficiency in such an embodiment is not supplied during the quiescent phases, which means that the handpiece, the cutting tip and the parts surrounding them can cool down by virtue of convection and/or heat exchange with the aspiration or irrigation fluid. During the entire emulsification process, low thermal loading is thus achieved for the eye, emulsification nevertheless being effected with a high level of efficiency. It is advantageous if the apparatus can be operated such that every second a number of quiescent phases can be attained which is at least 1 and is no more than the absolute value of 1 percent of the natural frequency of the handpiece. For a natural frequency of 40 kHz, these are therefore no more than 400 quiescent phases per second.

In addition, it may be advantageous if the energy supplied to the handpiece can be varied in level from one oscillation phase to the next oscillation phase. This means that it is possible to allow for the fact that there are clouded lenses of different hardness which require a different minimum supply of energy.

In line with another embodiment of the invention, the energy supplied by the amplifier can be regulated such that a first oscillation phase, in which the cutting tip is operated at an amplitude which can be used to emulsify the lens, is followed by a second oscillation phase, in which the cutting tip is operated at an amplitude which cannot be used to emulsify the lens. During the second oscillation phase, the supply of energy is therefore not interrupted completely. Hence, when the second oscillation phase has elapsed, the oscillation onset time for the next oscillating phase for the emulsification can be shortened.

Preferably, the handpiece with the cutting tip has a natural frequency of between 20 and 100 kHz, particularly preferably of 40 kHz, and can be operated such that the cutting tip outputs a mechanical power of between 0 and 3.4 watts during emulsification.

The object is also achieved by a method for operating the aforementioned phacoemulsification apparatus, wherein energy supplied by the amplifier is repeatedly interrupted completely, so that a respective oscillation phase is followed by a quiescent phase. This prompts a reduction in the thermal loading for the parts which are heated by the ultrasonic oscillations. It is handy if the apparatus is operated such that every second there is a number of quiescent phases which is at least 1 and is no more than the absolute value of 1 percent of the natural frequency of the handpiece.

In line with a further embodiment of the method according to the invention, the energy supplied by the amplifier is regulated such that a first oscillation phase, in which the cutting tip is operated at an amplitude which can be used to emulsify the lens, is followed by a second oscillation phase, in which the cutting tip is operated at an amplitude which cannot be used to emulsify the lens. As a result, a shorter time is required for lowering the amplitude of the cutting tip from a maximum value to a value which is insignificant for the emulsification. Similarly, a shorter time is required for increasing it quickly again to a maximum value for the amplitude from this low-amplitude value.

Preferably, in line with one development of the method according to the invention, the energy supplied to the handpiece is varied in level from one oscillation phase to the next oscillation phase. In line with a further embodiment, the energy required for the second oscillation phase is formed from a residual energy which comes from the energy supplied during the first oscillation phase.

It is also advantageous if the piezo elements which are in white noise or which are oscillating only at low amplitude are excited by an electrical pulse such that a larger oscillation amplitude for the cutting tip is achieved in comparison with white noise or the oscillation at low amplitude. This allows better signal processing to be achieved.

The object is also achieved by a phacoemulsification system having a phacoemulsification apparatus as described above, an irrigation apparatus, an aspiration apparatus and a control apparatus for operating the phacoemulsification apparatus, the irrigation apparatus and the aspiration apparatus.

Further advantages and exemplary embodiments of the invention are explained in more detail below with reference to schematic drawings, in which.

Figure 1:
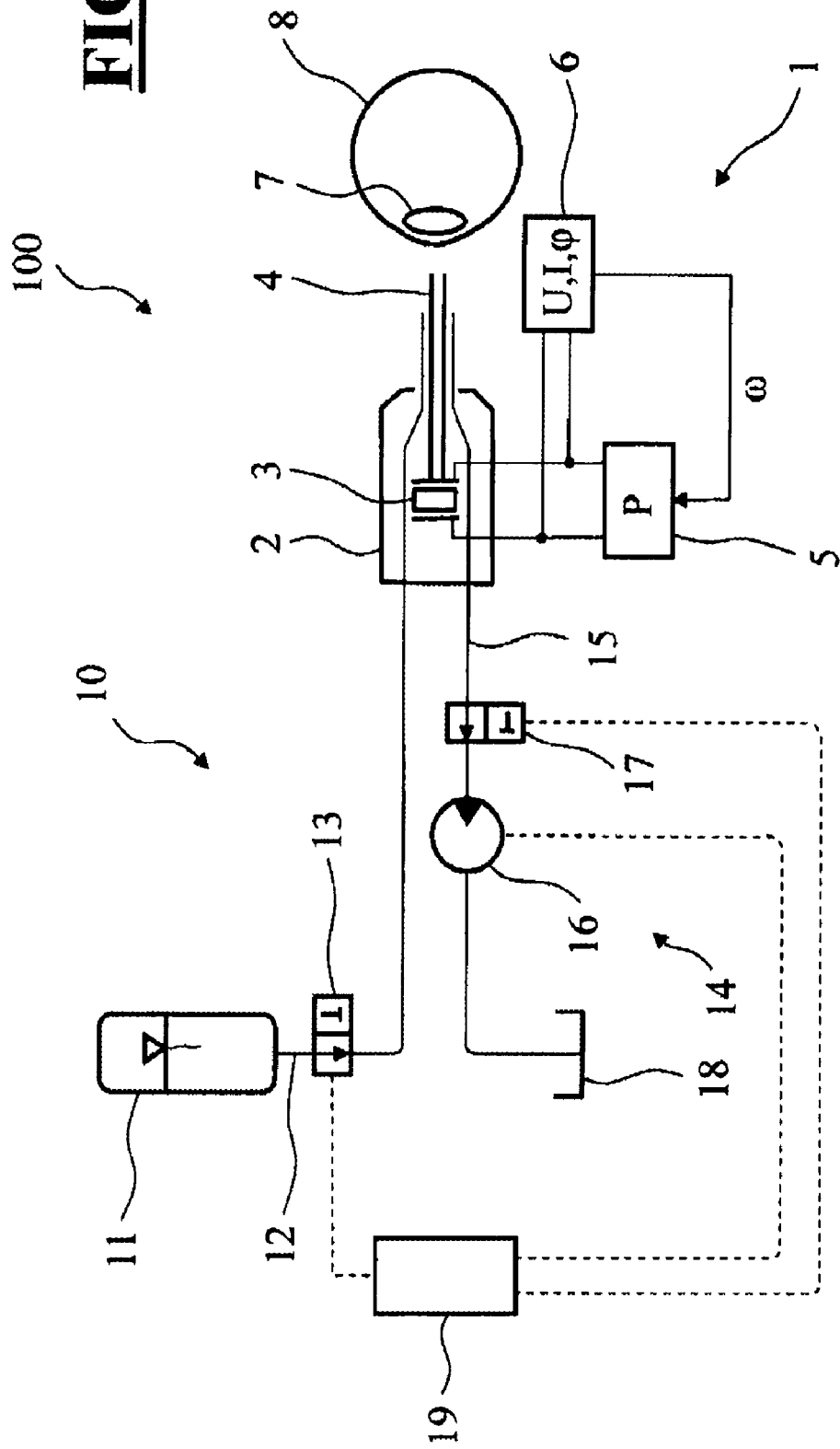
FIG. 1 shows a schematic illustration of a phacoemulsification system according to the prior art.

FIG. 1 schematically shows a system 100 for phacoemulsification. The system has a phacoemulsification apparatus 1 which has a handpiece 2, piezoceramic elements 3 contained therein and a cutting tip 4 coupled thereto. The piezoceramic elements 3 are connected to a power supply 5 which is suitable for prompting longitudinal expansion of the piezoceramic elements 3. The voltage and current profiles as a function of time and the associated phase angle φ are sensed using the controller 6, wherein the excitation frequency ω is changed such that the phase angle φ is provided with the lowest possible absolute value. This signal with the altered excitation frequency ω is supplied to the power supply 5, which operates the piezoceramic elements 3 as appropriate. The phacoemulsification apparatus 1 is connected to an irrigation system 10 and an aspiration system 14. The irrigation system 10 has an irrigation container 11 with an irrigation line 12 leading away, the intake of which can be controlled by an irrigation valve 13. The irrigation fluid flows via the cutting tip 4 to an eye 8 with the lens 7 which is to be treated. When the cutting tip 4 emulsifies the lens 7 by means of ultrasonic oscillations, the irrigation fluid and the emulsified particles are transported away by the aspiration system. This is done via a line 15 which is connected to an aspiration pump 16, the flow through the line 15 being able to be separated by means of an aspiration valve 17. The aspirated fluid and the emulsified particles are then supplied to a container 18. The valves 13 and 17 and the pump 16 are operated by means of a control apparatus.

Figure 2:
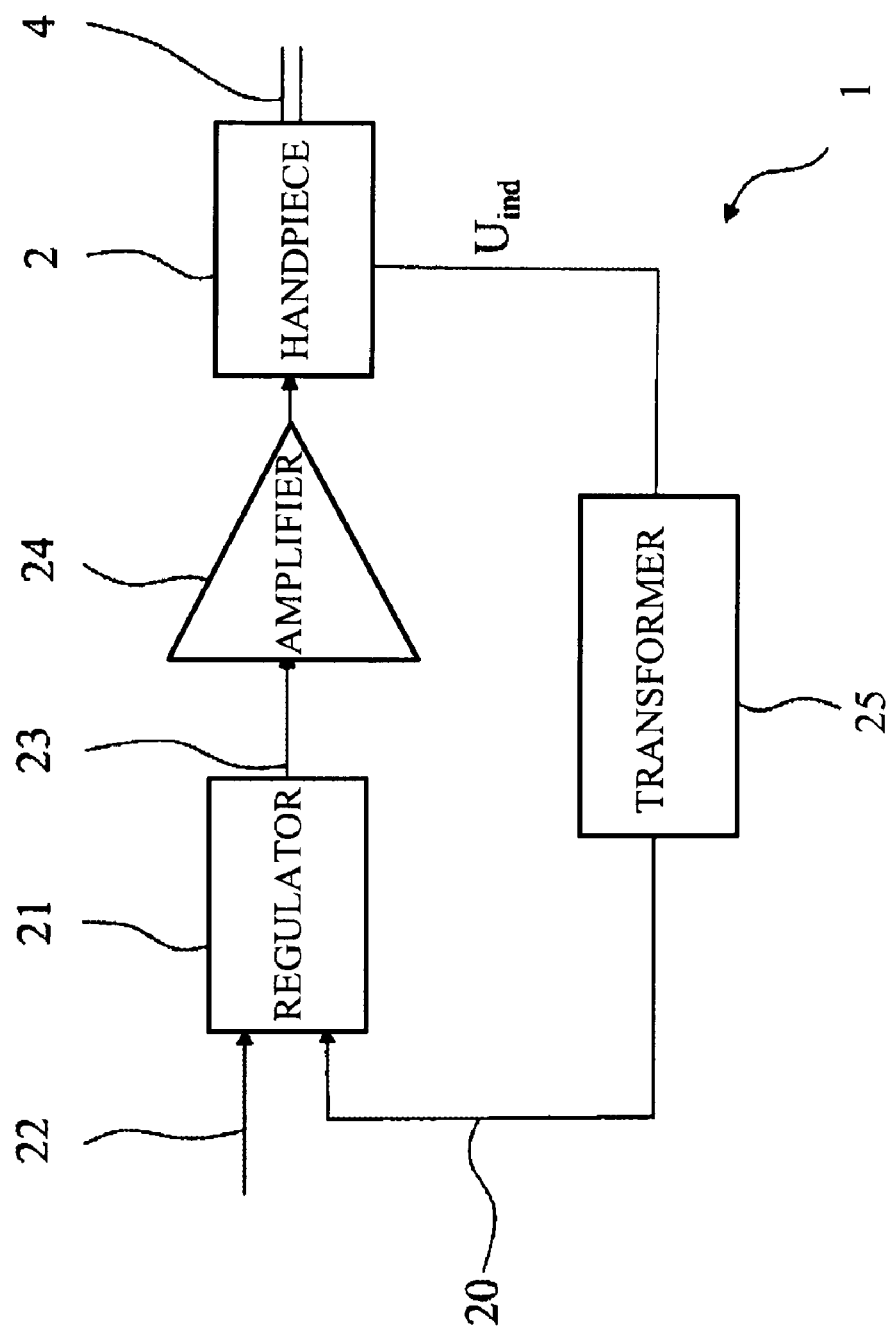
FIG. 2 shows a schematic illustration of a phacoemulsification apparatus according to the invention.

In the phacoemulsification apparatus 1 according to the invention, no phase shift φ is sensed between a voltage profile and a current profile. Instead, an actual value is sensed which is proportional to the voltage, induced in the piezoelectric elements, of the handpiece 2 oscillating at the natural frequency, said actual value being supplied to a regulator 21 via a line 20, see FIG. 2. The regulator 21 is suitable for comparing a prescribed target value 22, for example a voltage which represents an oscillation amplitude which is prescribed by a user using a foot pedal, with the actual value and then determining a controlled variable 23 which is supplied to a power amplifier 24. The output of the power amplifier 24 is connected to the handpiece, so that the handpiece can oscillate at its natural frequency with amplified deflection of the cutting tip.

This amplified oscillation in turn induces a voltage which is amplified by direct feedback in the same way as described above. A closed control loop of this kind increases the amplitude of the cutting tip after a few passes, said cutting tip always oscillating at its natural frequency.

After a short time, the amplitude can become so large that what is known as a resonance disaster occurs, so that the piezo ceramics are no longer able to transmit the amplitudes and become damaged. To prevent this, suitable power regulation need to be provided. When a resonance disaster is threatening, it is therefore possible to set the gain factor of the power amplifier to less than 1. In this case, the phacoemulsification apparatus according to the invention can be operated such that the amplitude of the cutting tip is always constant in the face of changing conditions, for example as a result of heating, ageing of the components and a change of mass on account of the respective lens fragments. The amplitude of the cutting tip is respectively directly proportional to the induced voltage which is used as a control variable.

As described in "IEC NWIP Requirements for lens removal and vitrectomy devices for ophthalmic surgery, 201.12.4.101.7 Hazardous output for ultrasonic average velocity of TIP", the maximum admissible speed of the cutting tip is limited to 20 m/s. It is therefore possible for an induced voltage proportional to the amplitude to be prescribed for the regulator 21 as a target limit value.

In the quiescent state, the handpiece 2 oscillates with its cutting tip 4 at its natural frequency, the amplitude being very small. This state is referred to as what is known as "white noise". Should the induced voltage generated on the basis of this very small amplitude be too low for further processing with the regulator 21, the handpiece can be excited to oscillation by an external pulse, so that a higher amplitude and induced voltage are attained. However, the induced voltages may also be relatively high, so that they are no longer suitable for further processing with the regulator 21. For this reason, a transformer 25 may also be provided which brings about transformation of the voltages, with a high signal transmission rate being assured.

The conversion of electrical to mechanical energy in the handpiece produces heat. Such heat can be transmitted from the cutting tip to the cornea and to the clouded lens and may be a danger to the cornea (cornea burn), for example. It is therefore advantageous if, at the highest possible efficiency of emulsification, the additionally produced heat can be reduced to a minimum. This can be achieved firstly by optimizing the level of efficiency, as is possible in the case of the phacoemulsification apparatus according to the invention. A further measure may involve the supplied energy as a whole being consciously kept down. So as nevertheless to achieve emulsification of the lens, a minimum energy needs to be supplied. If the supplied energy is below a threshold value, only heat is introduced into the eye, with emulsification not taking place. Above such a threshold, emulsification takes place, and it is then dependent on the number of oscillation periods before breakup of the lens is achieved. The phacoemulsification apparatus according to the invention can therefore be operated such that sufficiently high amplitudes for emulsifying the lens are taken as a basis for actuating the cutting tip such that the supply of energy is interrupted completely. An oscillation phase is therefore followed by a quiescent period in which oscillation based on white noise occurs, but in unaltered form.

Figure 3:
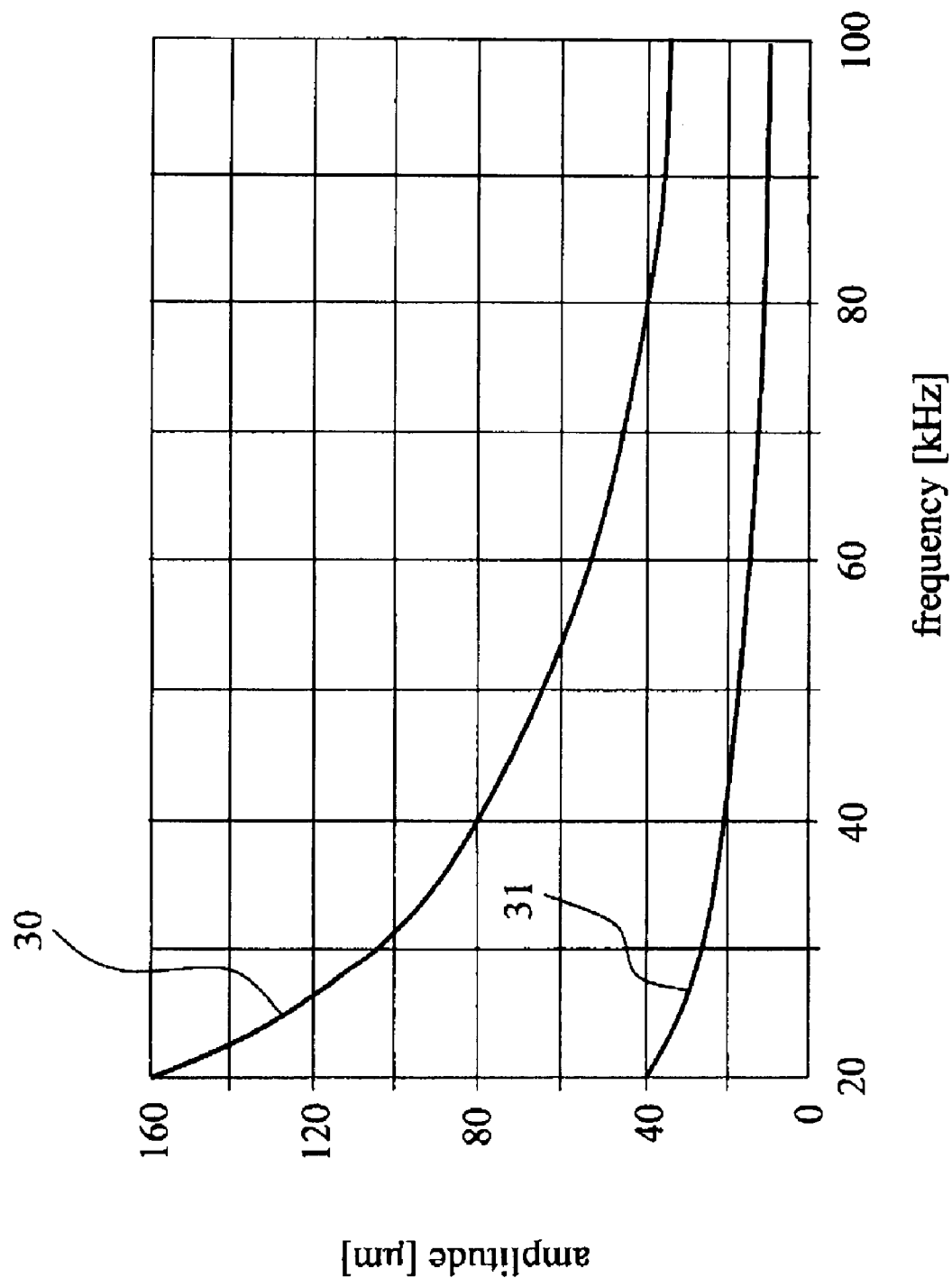
FIG. 3 shows a graph with a profile for the maximum and minimum amplitudes of the cutting tip as a function of the frequency thereof.

FIG. 3 shows the respective admissible amplitude of the cutting tip as a function of time for an embodiment of the invention. This illustration takes account of the fact that the maximum speed of the cutting tip is 20 m/s. If the cutting tip is operated at a frequency of 40 kHz, for example, then the maximum admissible amplitude is 80 μm, see curve 30. The minimum amplitude at a frequency of 40 kHz is approximately 20 μm, see curve 31, with operation at an even smaller amplitude resulting merely in low heating, but no longer in emulsification of the lens. If the cutting tip is operated at a maximum amplitude $s_{max}$, the maximum longitudinal stress $\sigma_{max}$ in the lens to be emulsified is calculated on the basis of $$\sigma_{max} = \rho \omega^2 s_{max}^2 \tag{1}$$

In this case, the density ρ of the lens material is assumed to be 1000 kg/m³, where w is the angular frequency and $s_{max}$ is the maximum amplitude of the cutting tip. At a frequency f=w/2n=40 kHz and a maximum amplitude of $s_{max}$=80 μm, the maximum longitudinal stress $\sigma_{max}$ is approximately 0.4 MPa. The hardness or the fracture resistance of the lens of the eye can be taken as a basis for choosing a suitable amplitude for the cutting tip. If the chosen amplitude involves the fracture resistance of the lens of the eye being reached or exceeded, a single deflection of the cutting tip is sufficient to break up a lens fragment. The hardness of the lens of the eye can vary a great deal, however, and may also be so hard that break-up is not achieved until deflection of the cutting tip is repeated. The minimum deflection for emulsification is calculated on the basis of $$s_{min} = (\epsilon E/\rho \omega^2)^{1/2}$$

wherein $s_{min}$ signifies the minimum deflection, $\epsilon$ signifies the expansion of the lens material and E signifies the modulus of elasticity of the lens material. In addition, $\rho$ is the density of the lens material and w is the angular frequency. If $\epsilon = 0.3$, $E = 0.084$ N/mm$^2$, $\rho = 1000$ kg/m$^3$ and w=2nf where f=40 kHz then the minimum deflection is obtained at approximately 20 µm, which means that the ratio of minimum to maximum deflection is approximately 25%.

The mechanical power of the cutting tip which is transmitted to the lens can be calculated on the basis of the following equation:

$$P = \rho \pi^4 (D^2 - d^2) f^3 s^3 \qquad (3)$$

In this case, $\rho$ is the density of the lens material, D is the external diameter of the tubular cutting tip, d is the internal diameter of the cutting tip, f is the natural frequency of the handpiece with the cutting tip, and s is the amplitude of the cutting tip. If the numerical values used are density $\rho = 1000$ kg/m$^3$, D=1.2 mm, d=0.6 mm, f=40 kHz and s=80 µm then a maximum mechanical power of $P_{max} = 3.4$ W is obtained. If only a minimum amplitude of approximately 20 µm (see FIG. 3) is provided, the mechanical power $P_{min}$ is now only 0.054 W, that is to say approximately 1.6% of the maximum absolute value. If less than 0.054 W is supplied, emulsification no longer takes place, but rather now only relatively slight heating of the lens. If a higher mechanical power than 3.4 W is supplied, the prescribed limit value for a maximum speed of 20 m/s for the cutting tip is exceeded.

Figure 4:
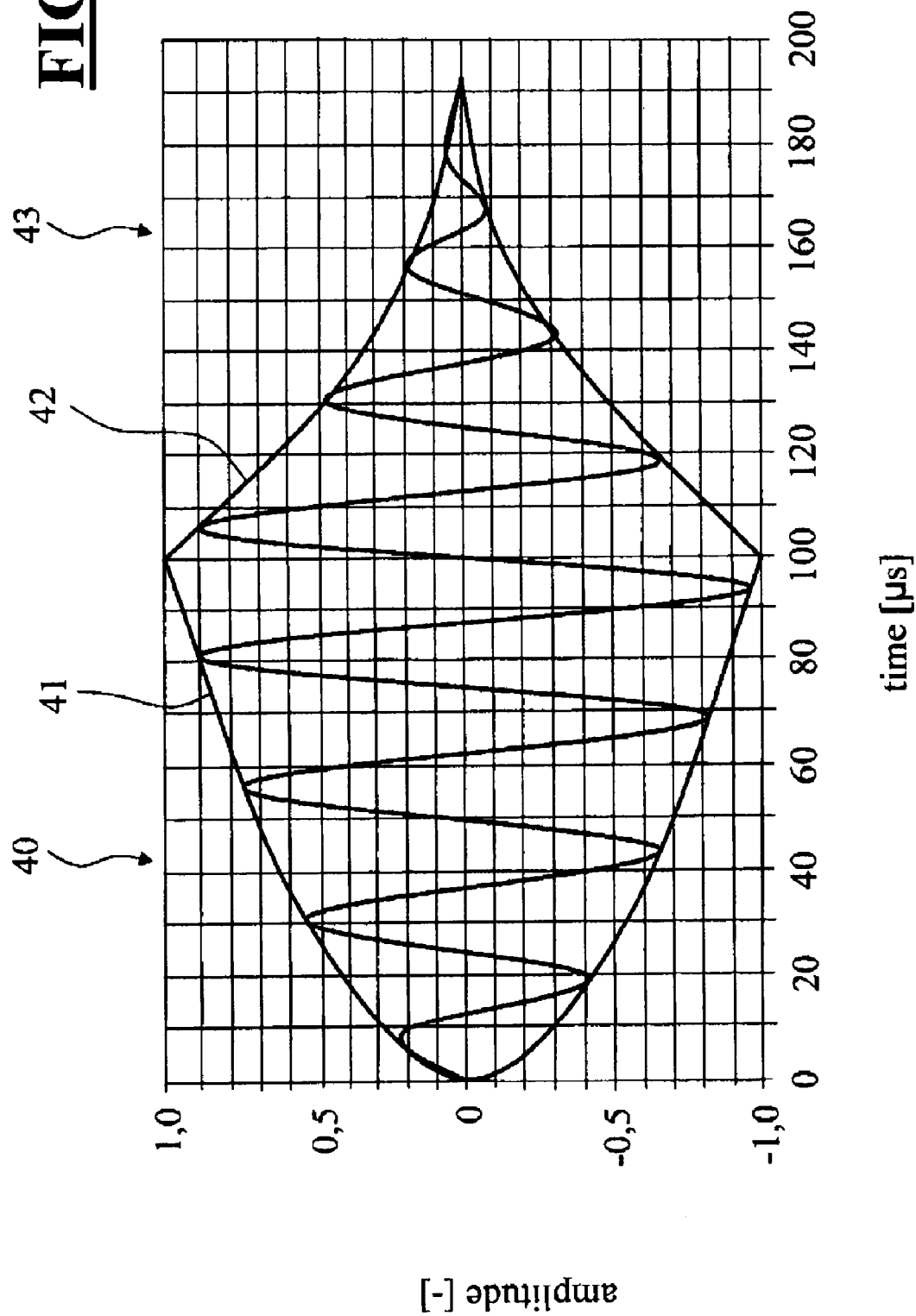
FIG. 4 shows a graph to illustrate an oscillation onset and oscillation decay response for the phacoemulsification apparatus according to the invention.

It is important to the operator for the lens of the eye to be emulsified in the shortest possible time with low thermal loading. It is therefore advantageous for the operation of the cutting tip to be implemented with as large a mechanical amplitude as possible, so as subsequently to provide quiescent phases for cooling the aforementioned components. The process of oscillation onset until the maximum amplitude is reached and of oscillation decay until a deflection to the value 0 is reached is shown by the graph in FIG. 4. The cutting tip oscillates at a natural frequency in each case, with the amplitudes constantly increasing during the oscillation onset process 40 (see the profile of the envelope 41). When the maximum amplitude has been reached, interruption to the supply of energy can result in a rapid decrease in the level of the amplitudes, see envelope 42. In the example shown in FIG. 4, the amplitude decreases to the absolute value 0 after approximately 4 oscillation periods during the oscillation decay process 43. The requisite time for the oscillation onset and oscillation decay processes is dependent on the frequency of the cutting tip. At a high frequency, the maximum amplitude is reached more quickly than at a low frequency.

For optimum emulsification, both the amplitude of the oscillation and the oscillation time can be altered. In the example shown in FIG. 5, the maximum amplitude is reached after four oscillation periods, see envelope 50. There then follow ten oscillation periods, see reference symbol 51, in which the cutting tip can act on the lens. When these ten oscillation periods have elapsed, see reference symbol 52, the supply of energy is interrupted, so that the amplitude of the cutting tip rapidly decreases, see envelope 53. After approximately four further oscillation periods, the amplitude of the cutting tip has reached the absolute value 0, see reference symbol 54. In this context, what is important is that the oscillation is respectively effected, from start to end, at a natural frequency of the handpiece with the cutting tip.

Figure 6:
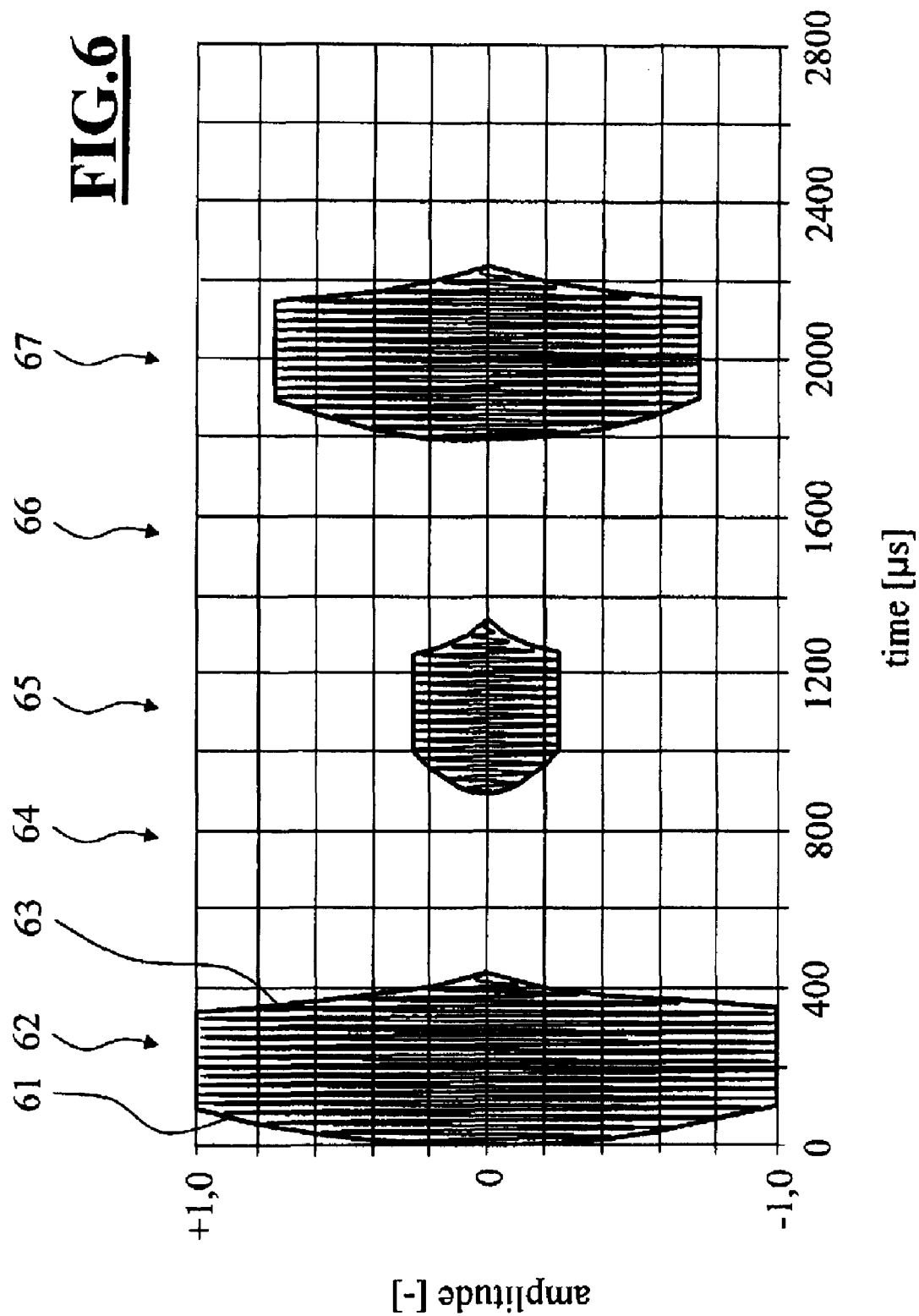
FIG. 6 shows a graph for an embodiment of the method according to the invention for operating the phacoemulsification apparatus.

When the amplitude of the cutting tip has reached the absolute value 0, the supply of energy to the piezoceramic elements can remain interrupted for a certain period of time. When such a quiescent phase has elapsed, an oscillation phase can again follow, see FIG. 6. During a first oscillation phase, the amplitude of the cutting tip increases up to its maximum absolute value, see envelope 61, and it subsequently remains at this maximum amplitude for a period of time covering a plurality of oscillation periods, see reference symbol 62. The supply of energy is then interrupted, so that the amplitude of the cutting tip decreases to 0, see envelope 63. There then follows a quiescent phase 64, which is followed by a second oscillation phase, see reference symbol 65. In this context, the amplitude in this second oscillation phase 65 may be lower than in the first oscillation phase 62. This may again be followed by a quiescent phase 66 which is in turn followed by a next oscillation phase 67. During this oscillation phase 67, an amplitude can be chosen which differs from the amplitude during the first oscillation phase 62 and/or the second oscillation phase 65.

To achieve a faster rise until the maximum amplitude is reached, in another embodiment of the method for operating the phacoemulsification apparatus, the phacoemulsification apparatus can be operated at a low oscillation amplitude even during a quiescent phase 64 or 66, so that the handpiece is not totally at rest. The supplied power is relatively low in this period of time, and the heating is negligible. By way of example, a residual energy can be used by returning energy. The advantage of this method is that the cutting tip can be regulated from an oscillation at low amplitude to an oscillation at relatively high amplitude more quickly. Again, it is pointed out that during the oscillation phases the handpiece with the cutting tip oscillates at its natural frequency in each case.

Figure 5:
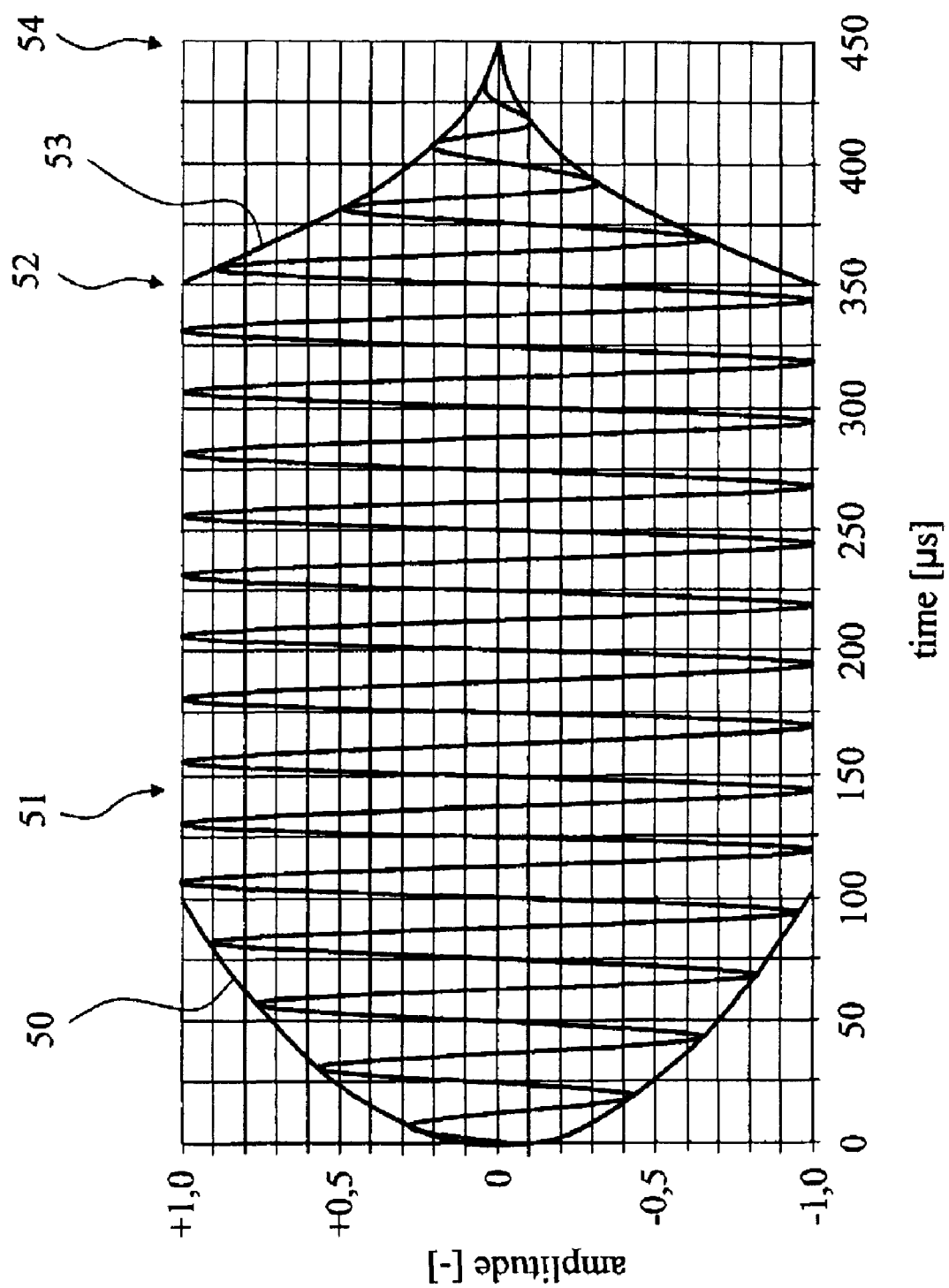
FIG. 5 shows a graph showing an oscillation process during operation of the phacoemulsification apparatus according to the invention.
Figure 7:
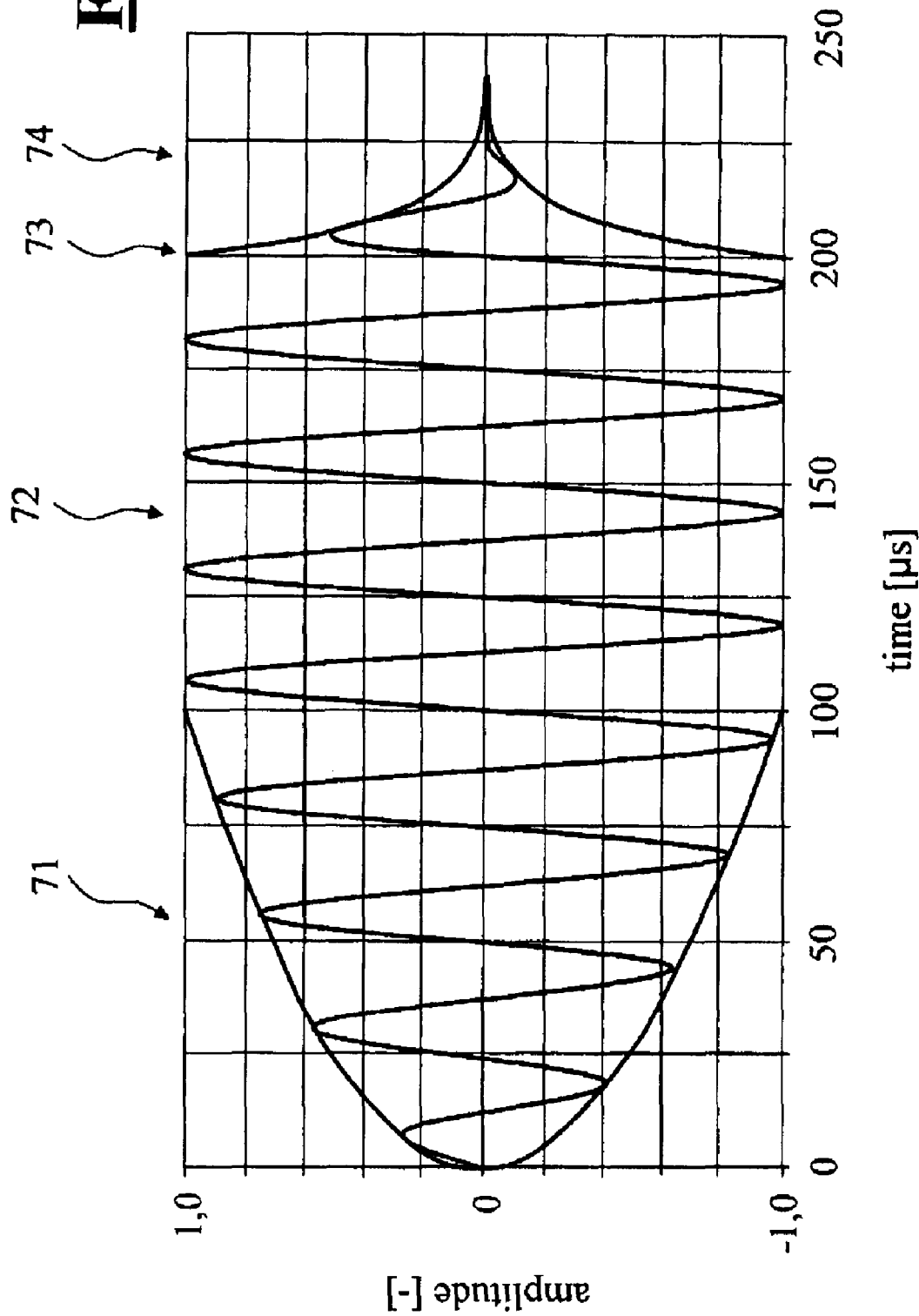
FIG. 7 shows a graph for a further embodiment of the method according to the invention for operating the phacoemulsification apparatus.

In line with a further embodiment of the method for operating the phacoemulsification apparatus, a short circuit reduces the oscillation decay time, see FIG. 7. After an oscillation onset condition, see reference symbol 71, the cutting tip oscillates for a further 4 periods, for example, see reference symbol 72. When the supply of energy has been switched off, see reference symbol 73, and the energy still present has been discharged in targeted fashion, the time 74 for the oscillation decay of the cutting tip is shorter than in the case of a normal oscillation decay process, as shown in FIG. 5, for example.

If an occlusion or an occlusal eruption occurs during phacoemulsification, the natural frequency changes for a short time. Such a frequency shift can be used in order to detect such an event. The phacoemulsification apparatus according to the invention therefore allows such a process to be detected very quickly, so that further subsystems, such as a fluid system, can be actuated very quickly. This attains a high level of stability in the eye, inter alia.

The invention claimed is:
1. A phacoemulsification apparatus, comprising:
  a handpiece comprising:
    a cutting tip configured to emulsify a lens; and
    piezoelectric elements configured to deflect the cutting tip;
  a regulator electrically connected to the handpiece to receive an actual value which is proportional to a voltage induced on the piezoelectric elements when the handpiece is constantly oscillating at its natural frequency, the regulator being configured to compare the actual value with a prescribed target value to determine a controlled variable; and a power amplifier having its input connected to the regulator to receive the controlled variable, and the power amplifier having its output connected to the handpiece, wherein, at the same time that the actual value is received by the regulator, the handpiece can be actuated and power can be output to the handpiece, so that direct feedback can be achieved and the handpiece can constantly oscillate at its natural frequency with deflection of the cutting tip in line with the controlled variable.

2. The phacoemulsification apparatus as claimed in claim 1, further comprising a transformer, the transformer having its output connected to the regulator and the transformer having its input connected to the handpiece.

3. The phacoemulsification apparatus as claimed in claim 1, wherein the piezoelectric elements can be excited by an electrical pulse such that a larger oscillation amplitude for the cutting tip is achieved in comparison with white noise.

4. The phacoemulsification apparatus as claimed in claim 1, wherein energy supplied by the amplifier can be repeatedly interrupted completely, so that a respective oscillation phase is followed by a quiescent phase.

5. The phacoemulsification apparatus as claimed in claim 4, wherein the apparatus can be operated such that every second a number of quiescent phases can be attained which is at least 1 and is no more than the absolute value of 1 percent of the natural frequency of the handpiece.

6. The phacoemulsification apparatus as claimed in claim 4, wherein the energy supplied to the handpiece can be varied in level from one oscillation phase to the next oscillation phase.

7. The phacoemulsification apparatus as claimed in claim 1, wherein energy supplied by the amplifier can be regulated such that a first oscillation phase, in which the cutting tip is operated at an amplitude which can be used to emulsify the lens, is followed by a second oscillation phase, in which the cutting tip is operated at an amplitude which cannot be used to emulsify the lens.

8. The phacoemulsification apparatus as claimed in claim 1, wherein the handpiece with the cutting tip has a natural frequency of between 20 and 100 kHz.

9. The phacoemulsification apparatus as claimed in claim 1, wherein the cutting tip can be operated such that it outputs a mechanical power between 0 and 3.4 watts.

10. A method, comprising:
operating the phacoemulsification apparatus as claimed in claim 1, wherein the energy supplied by the amplifier is repeatedly interrupted completely, so that a respective oscillation phase is followed by a quiescent phase.

11. The method as claimed in claim 10, wherein the apparatus is operated such that every second there is a number of quiescent phases which is at least 1 and is no more than the absolute value of 1 percent of the natural frequency of the handpiece.

12. The method as claimed in claim 1, wherein the energy supplied to the handpiece is varied in level from one oscillation phase to the next oscillation phase.

13. A method, comprising:
operating the phacoemulsification apparatus as claimed in claim 1, wherein the energy supplied by the amplifier is regulated such that a first oscillation phase, in which the oscillation phase is operated at an amplitude which can be used to emulsify the lens, is followed by a second oscillation phase, in which the cutting tip is operated at an amplitude which cannot be used to emulsify the lens.

14. The method as claimed in claim 13, wherein the energy required for the second oscillation phase is formed from a residual energy which comes from the energy supplied during the first oscillation phase.

15. A method, comprising:
operating the phacoemulsification apparatus as claimed in one claim 1, wherein the piezoelectric elements are excited by an electrical pulse such that a larger oscillation amplitude for the cutting tip is achieved in comparison with white noise.

16. A phacoemulsification system, comprising:
a phacoemulsification apparatus as claimed in claim 1,
an irrigation apparatus,
an aspiration apparatus, and
a control apparatus configured to operate the phacoemulsification apparatus, the irrigation apparatus and the aspiration apparatus.

17. The phacoemulsification system of claim 16, further comprising a transformer having its output connected to the regulator and the transformer having its input connected to the handpiece.

18. The phacoemulsification system of claim 16, wherein the piezoelectric elements can be excited by an electrical pulse such that a larger oscillation amplitude for the cutting tip is achieved in comparison with white noise.

19. The phacoemulsification system as claimed in claim 16, wherein energy supplied by the amplifier can be repeatedly interrupted completely, so that a respective oscillation phase is followed by a quiescent phase.

20. The phacoemulsification system as claimed in claim 19, wherein the apparatus can be operated such that every second a number of quiescent phases can be attained which is at least 1 and is no more than the absolute value of 1 percent of the natural frequency of the handpiece.

* * * * *

UNITED STATES PATENT AND TRADEMARK OFFICE
CERTIFICATE OF CORRECTION

PATENT NO. : 8,277,462 B2
APPLICATION NO. : 12/677690
DATED : October 2, 2012
INVENTOR(S) : Manfred Heymann Page 1 of 1

It is certified that error appears in the above-identified patent and that said Letters Patent is hereby corrected as shown below:

Column 6,
Line 58, delete "w" and insert --$\omega$--

Column 6,
Line 60, delete "f=w/2n=40" and insert --$f=\omega/2\pi=40$--

Column 7,
Line 5, delete "$S_{min}=(\varepsilon E/\rho\omega^2)^{1/2}$" and insert --$S_{min}=(\varepsilon E/\rho\omega^2)^{1/2}$       (2)--

Column 7,
Line 10, delete "w" and insert --$\omega$--

Column 7,
Line 11, delete "W=2nf" and insert --$\omega=2\pi f$--

Column 10,
Line 6, delete "1" and insert --10--

Column 10,
Line 23, before "claim" delete "one"

Signed and Sealed this
Twelfth Day of February, 2013

Teresa Stanek Rea
*Acting Director of the United States Patent and Trademark Office*